United States Patent [19]

Weightman et al.

[11] Patent Number: 4,680,026

[45] Date of Patent: Jul. 14, 1987

[54] SUCTION-IRRIGATION EQUIPMENT HAVING A RECIPROCATING VALVE

[76] Inventors: Barry O. Weightman, 26, Basing Way, Thames Ditton, Surrey; Graham Deane, "Oakwood", Burleigh Rd., Ascot, Berkshire, both of England

[21] Appl. No.: 838,449

[22] Filed: Mar. 11, 1986

Related U.S. Application Data

[63] Continuation of Ser. No. 730,259, May 6, 1985, abandoned, which is a continuation of Ser. No. 473,505, Mar. 8, 1983, abandoned.

[30] Foreign Application Priority Data

Mar. 29, 1982 [GB] United Kingdom ............... 8209132

[51] Int. Cl.$^4$ ............................................. A61M 1/00
[52] U.S. Cl. ........................................ 604/33; 433/84; 433/95; 604/902
[58] Field of Search .............. 604/30, 32, 33, 27, 604/28, 29, 30, 32–35, 48, 54, 118, 119, 902, 249; 433/84, 85, 91, 92, 95, 100; 137/625.4, 625.5, 625.48, 625.69

[56] References Cited

U.S. PATENT DOCUMENTS

| | | | |
|---|---|---|---|
| 1,172,833 | 2/1916 | Ricker | 137/625.5 |
| 1,843,169 | 2/1932 | McKesson | 604/902 |
| 2,669,233 | 2/1954 | Friend | 604/33 |
| 2,812,765 | 11/1957 | Tofflemire | 604/32 |
| 2,874,696 | 2/1959 | Brief | 604/34 |
| 3,279,748 | 10/1966 | Coulter | 137/625.69 |
| 3,678,959 | 7/1972 | Liposky | 604/33 |
| 4,036,210 | 7/1977 | Campbell | 604/33 |
| 4,047,527 | 9/1977 | Kelsen | 604/249 |
| 4,193,406 | 3/1980 | Jinotti | 604/33 |
| 4,261,343 | 4/1981 | Ouchi et al. | 128/4 |
| 4,334,538 | 6/1982 | Juhn | 433/95 |
| 4,408,598 | 10/1983 | Veda | 128/4 |
| 4,416,658 | 11/1983 | Numazawa et al. | 604/902 |
| 4,451,257 | 5/1984 | Atchley | 604/902 |
| 4,526,573 | 7/1985 | Lester et al. | 604/902 |

FOREIGN PATENT DOCUMENTS 421024 12/1934 United Kingdom .
422966 1/1935 United Kingdom .

Primary Examiner—C. Fred Rosenbaum
Assistant Examiner—J. L. Kruter
Attorney, Agent, or Firm—Pollock, VandeSande and Priddy

[57] ABSTRACT

A hand-held suction-irrigator, particularly for surgical use, has a handle and two inlet bores extending through the handle and connected respectively to a suction source and a source of irrigating fluid. A valve assembly connects one or the other of the bores to a single outlet port so that the outlet port can be used to apply suction or irrigating fluid. A probe is removably coupled to the outlet port by cooperating luer fittings. The two inlet bores are parallel with one another, the outlet port being located intermediate the inlet bores on the opposite side of the valve assembly. A valve member is mounted in the valve assembly and can be displaced transversely of the bores by pushing down on the valve member with a finger or thumb.

5 Claims, 7 Drawing Figures

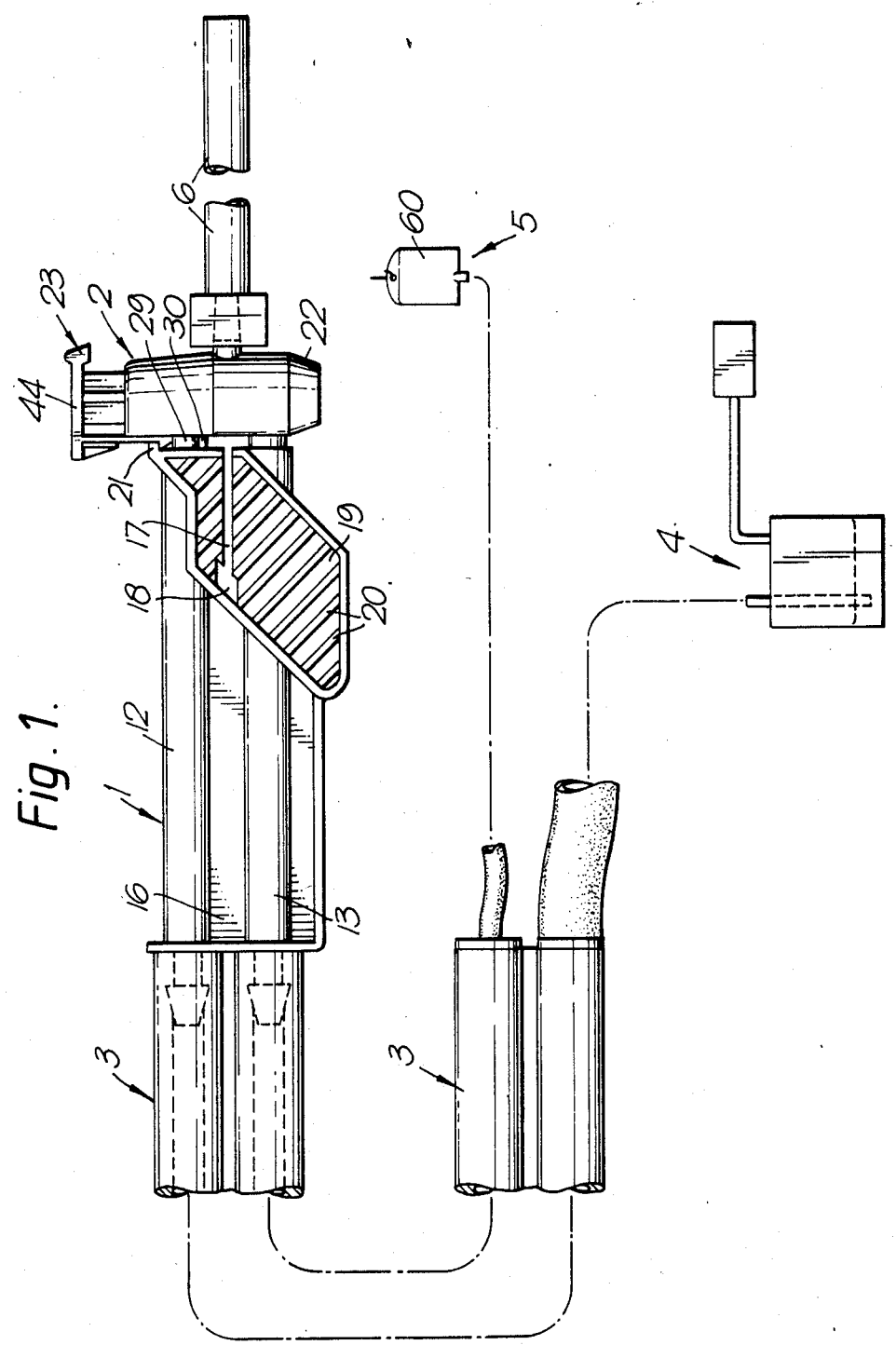

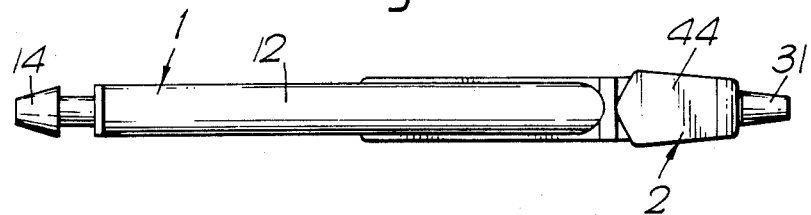
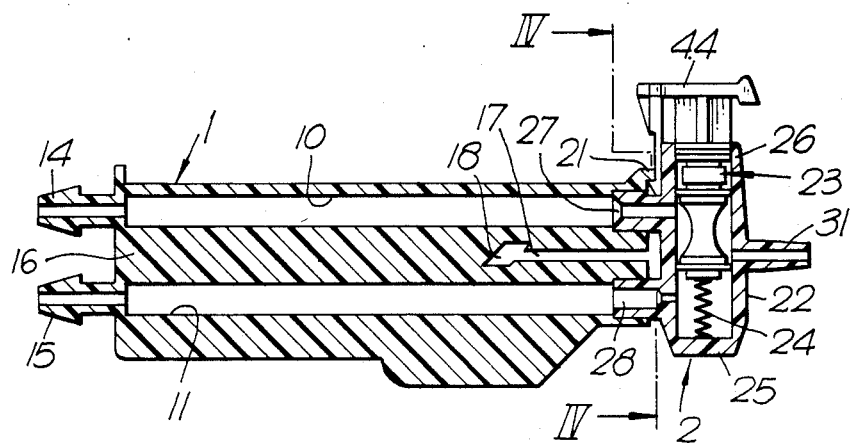
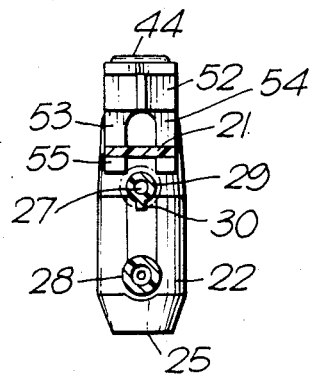

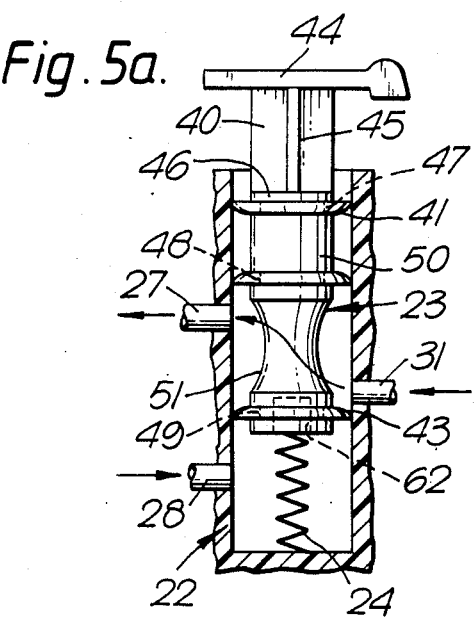
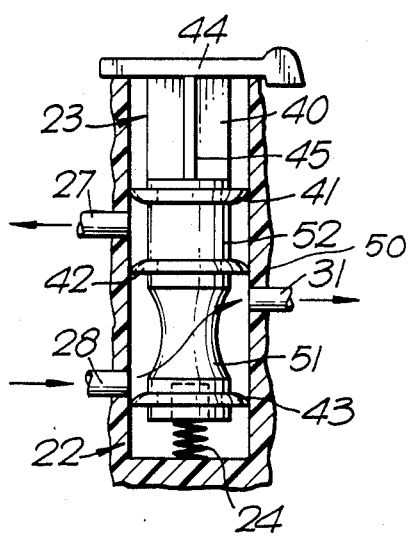
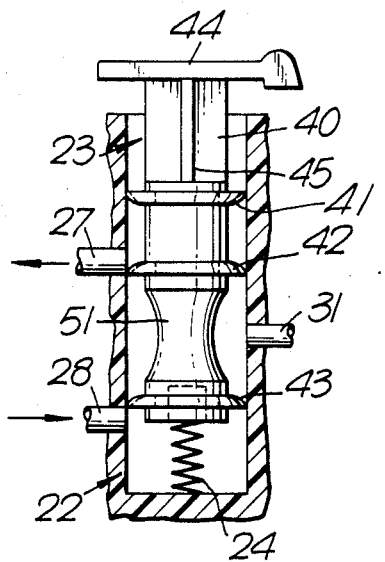

ered within respective bores at the forward end of the double
SUCTION-IRRIGATION EQUIPMENT HAVING A RECIPROCATING VALVE This application is a continuation, of application Ser. No. 730,259, filed May 6, 1985, now abandoned, which is a continuation, of application Ser. No. 473,505, filed Mar. 8, 1983, now abandoned.

BACKGROUND OF THE INVENTION

The invention relates to suction-irrigation equipment.

The invention is more particularly concerned with suction-irrigation equipment for hand-held medical use, such as, of the kind used for cleaning wounds during surgery.

During surgery it is often necessary to drain and wash the site of a wound. This is usually accomplished by means of a hand-held suction irrigator that is easily manoeuvrable to direct irrigating fluid (such as sterile water or saline solution) onto the precise location and to remove unwanted substances in the same way. The previous equipment used for this purpose has two conduits that extend to its operating tip, one conduit being used for supply of irrigating fluid and the other for suction. One or both of the conduits may be continuously operating or the equipment may be provided with suitable valves so that the equipment may be used in a suction-only or irrigation-only mode. Examples of suction irrigators are described in UK patent specification No. 1 470 153 and UK patent application publication No. 2 058 576A.

Previous equipment can suffer from various disadvantages. One problem arises from the blockages that can often be caused by matter collecting in the suction conduit. These blockages can be difficult to remove and may make it necessary to replace equipment. Obviously this is to be avoided, especially during surgery where the equipment may be urgently needed. Also, if the suction conduit is brought too close to loose tissue this will be sucked towards the tip of the conduit and, while it may not be drawn into the conduit it can be held at the tip, even if the suction conduit is subsequently cut off from the suction source. Removal of the tissue would be achieved by pulling the equipment away from it until the force is sufficient to overcome the residual vacuum in the conduit. It will be appreciated that this can cause damage and injury to the patient. However, it could be useful to be able to use the suction conduit for picking up and transferring tissue or other matter if it could be removed readily. Up to now this has not been possible.

Other disadvantages of previous equipment arise from the fact that suction and irrigation are carried out through separate conduits. The provision of two separate conduits renders the forward end of the equipment rather bulky and can make it difficult to position in confined regions. The fact that the tips of the suction and irrigation conduits are necessarily spaced from one another also can be a disadvantage since this makes it necessary to move the tip if it is desired to remove fluid following irrigation.

BRIEF SUMMARY OF THE INVENTION

It is an object of the present invention to provide suction-irrigation equipment that can be used to alleviate the above-mentioned disadvantages.

According to one aspect of the present invention there is provided hand-held suction-irrigation equipment including a first conduit adapted for connection to a suction source; a second conduit adapted for connection to a source of irrigating fluid; valve means connected with said first and second conduits; and a single outlet conduit connected with said valve means, wherein said valve means is operable by the finger or thumb of a user while the equipment is being held at a handle portion of the equipment thereby-to connect said first or second conduit to said outlet conduit such that said outlet conduit can be used both to apply suction or to supply irrigating fluid.

The equipment may include a probe member removably coupled with said outlet conduit, such as with cooperating luer-tapered portions. Said first conduit, said second conduit and said outlet conduit may be arranged substantially parallel with one another. The valve means may include a valve member that is displaceable transversely of said conduits. Said first and second conduits, and said outlet conduit may be located on opposite sides of said valve means, said outlet conduit being located intermediate said first and second conduits.

A suction-irrigation system including suction-irrigation equipment according to the present invention will now be described by way of example, with reference to the following drawings.

BRIEF DESCRIPTION OF THE DRAWINGS

FIG. 1 is a side elevation view of the suction-irrigation system;

FIG. 2 is a plan view of the suction irrigator shown in FIG. 1;

FIG. 3 shows the suction irrigator in section;

FIG. 4 is a sectional view along the line IV—IV of FIG. 3; and

FIGS. 5a, 5b and 5c show the valve of the suction irrigator in greater detail, in three different positions.

DETAILED DESCRIPTION

With reference to FIGS. 1 to 3, the suction irrigator is in two parts, namely, a handle 1 and a valve assembly 2. The suction-irrigation system comprises double tubing 3 which connects the suction irrigator with a suction source 4 and a source of irrigation fluid 5. A probe 6 is fitted to the valve assembly 2 which is operable to connect the probe to the suction source 4 or the source of irrigation fluid 5.

With reference now especially to FIG. 3, the handle 1 is a unitary assembly of a rigid plastics material and may be made as a two-part moulding. The handle 1 is of generally rectangular shape and has two cylindrical bores 10 and 11 which run along the handle from its rear end to its forward end through tubular formations 12 and 13. At their rear ends the bores 10 and 11 are terminated with tapered spigots 14 and 15 which are received within respective bores at the forward end of the double tubing 3. The tubular formations 12 and 13 are linked by a central flat land 16 that extends along the length of the handle 1. At its forward end, the land 16 is formed with a slit 17 that extends parallel to the tubular formations 12 and 13 and that is slightly enlarged at its rear end 18. A lozengeshape grip portion 19 (FIG. 1) is formed at the forward end of the handle 1 by raised ribs 20 extending across the tubular formations 12 and 13 and the land 16. Above the forward end of the upper tubular formation 12 the handle is formed with a small lip 21, the purpose of which will become apparent later.

The valve assembly 2 is shown most clearly in FIGS. 3 and 5a to 5c. The assembly comprises three parts: an outer housing 22, a valve member 23, and a spring 24. The housing 22 is a precision plastics injection moulding of generally cylindrical shape, having a closed lower end 25 and an open upper end 26. On one side of the housing 22 are provided a vacuum inlet port 27 and an irrigating fluid inlet port and 28 spaced apart along the housing, the lower port 28 being arranged to fit within the forward end of the irrigation fluid bore 11 while the upper port 27 is similarly received within the end of the suction bore 10. Both ports 27 and 28 are provided by short parallel conduits projecting from the housing 22, the upper conduit being waisted close to the body of the housing to form a portion 29 of reduced external diameter that is reinforced by a web 30 extending along its lower edge. From the other side of the housing 22 there extends an outlet conduit or port 31 which is positioned between the two inlet ports 27, 28 and parallel with them. The outer surface of the outlet conduit 31 is formed with a luer-taper for receiving the probe 6.

The three ports 27,28 and 31 communicate with the interior of the body of the housing 22 which is accurately dimensioned and of cylindrical shape. The interior of the housing 22 contains the valve member 23 and the spring 24, the spring bearing on the lower end 25 of the housing and acting to urge the valve member 23 upwardly, transversely of the ports 27,28 and 31.

The valve member 23 has a rigid plastics body or stem 40 on which are mounted three resilient, elastomeric sealing flanges 41,42 and 43 that contact the internal surface of the housing 22. At its upper end, the stem 40 has a flat horizontal plate 44 on which the user places his finger or thumb to displace the valve member against the action of the spring 24. Beneath the plate 44 the stem has a short portion 45 of cruciform shape that terminates in a flat circular plate 46. Below the plate 46 the valve stem is of circular cross-section and is provided with three annular grooves 47,48 and 49 in which the sealing flanges 41 to 43 respectively are mounted. The flanges 41 to 43 are each dished such that the outer edges of the middle and lower flanges 42 and 43 are normally below their inner edges, that is, are convex when viewed from above; the upper flange 41 is mounted the other way up so that its outer edge is above its inner edge, thereby being concave when viewed from above. The upper flange 41 and the middle flange 42 are separated by a short cylindrical section 50 of the valve stem 40. The middle flange 42 and the lower flange 43 are separated by a waisted section 51 of concave profile. At its lower end the stem 40 has a central recess 62 in which the upper end of the steel spring 24 is received.

At the other end of the valve stem 40, the top plate 44 is provided with a downwardly-extending catch member 52 of generally inverted 'U'-shape (FIG. 4). When the stem 40 is located in the housing 22, the catch member 52 extends between the outside of the housing and the forward end of the handle 1. The catch member 52 has two arms 53 and 54 which extend down opposite sides of the port 27 astride its portion 29 of reduced diameter. On their rear surfaces the arms 53 and 54 are both provided with a raised tooth 55 that is arranged to engage the lower edge of the lip 21 so as thereby to limit upward travel of the valve member 23.

The suction irrigator is readily assembled by joining the valve housing 22 with the handle 1. In this respect, an adhesive or solvent may be applied to the outer surface of the ports 27 and 28, or to the forward end of the bores 10 and 11 so that the two parts are securely joined. The valve member 23 and spring 24 may be assembled before or after the housing 22 has been joined to the handle 1 since the resilience of the catch member 52 enables it to be pushed downwardly over the lip 21 to snap into position.

The suction irrigator would normally be used with the removable probe 6. The probe 6 is a single-bore tube that is formed at its rear end with a Luer-tapered connector that can be push fitted over the outlet port 31. The probe 6 may be different shapes and sizes according to the use to which it is to be put. Preferably, the internal diameter of the probe is less than that of the port 31 so that any blockage that might occur takes place within the probe. In this way, the probe can be readily replaced if the blockage cannot be removed.

In its natural position, the valve stem 40 is urged to its upper limit of its travel by the spring 24 until the catch member 52 engages the lip 21. This position is shown in FIG. 5a and it can be seen that the lower flange 43 on the valve stem is situated intermediate the outlet port 31 and the irrigation port 28 thereby effectively sealing the irrigation port from the outlet port. The middle flange 42 is situated just above the suction port 27 so that fluid is enabled to flow between the outlet port 31 and the suction port around the waisted section 51 of the valve stem. In this position therefore suction is applied to the outlet port 31 and the probe 6.

When the valve member 23 is depressed fully by pushing on the plate 44, as shown in FIG. 5b, the middle flange 42 moves to a position intermediate the outlet port 31 and the suction port 27 whereas the lower flange 43 lies just below the irrigation port 28. In this position therefore the irrigating fluid is free to flow from the port 28 to the outlet port 31, and from there to the probe 6.

It is also possible to position the valve member 23 so that the outlet port 31 is sealed from both the irrigation and suction sources. This position is shown in FIG. 5c and relies on positioning the middle flange 42 just below the suction port 27, and the lower flange just above the irrigation port 28.

The sealing flanges 41 to 43 are oriented so as to improve the seal with the wall of the housing 22, more particularly, they are arranged so that the pressure exerted on either side of each flange operates to urge them into closer contact with the wall of the housing. In the suction position, shown in FIG. 5a, the pressure of irrigating fluid supplied to the lower port 28 will force the outer edge of the lower flange 43 upwards into a more flat shape. Flattening the flange 43 will tend to give it a greater external diameter thereby bringing its outer edge into closer contact with the wall of the housing 22. The suction applied to the upper port 27 will also tend to flatten the lower flange 43 but because the suction port 27 is open to atmosphere via the outlet port 31, the pressure above the lower flange 43 will be substantially the same as atmospheric pressure. The suction will tend to make the seal provided by the middle flange 42 less effective but any leakage past this flange will be stopped by the upper flange 41 which is oriented such as to give an improved seal when suction is applied beneath it.

In the irrigation position, shown in FIG. 5b, the lower flange 43 moves below the irrigation port 28 and trapped fluid beneath the flange, in the lower port of the housing 22 will tend to force the flange into closer contact with the housing. The effectiveness of the seal provided by the lower flange 43 is, however, not so important in the irrigation mode since any leakage past the flange will be contained within the housing. In this position, the suction port 27 is sealed off below by the middle flange 42 and above by the upper flange 41. These flanges 41 and 42 both present convex surfaces to the port 27 so that the reduced pressure in the chamber defined between the two flanges tends to deform them into closer contact with the housing 22.

In the neutral position shown in FIG. 5c, the suction ports 27 is also sealed between the upper and middle flanges 41 and 42, whilst the lower flange is situated just above the irrigation ports 28 so that it seals the irrigation conduit in the same manner as in the suction mode.

In the suction mode, the user simply places the tip of the probe 6 close to the material to be removed and this is drawn through the probe and the suction bore 10 into the appropriate bore of the double tubing 3. To irrigate, the user depresses the valve member 23 to its fullest extent and the irrigation fluid—which may be supplied from a suspended bag 60 of saline solution—passes out of the tip of the probe. Placement of the probe tip can, in some circumstances, be made easier by partially depressing the valve member to the neutral position shown in FIG. 5c so that the outlet port 31 is sealed off.

The suction irrigator can be used for picking up and placing material such as tissue. To do this, the equipment is placed in the suction mode and the tip of the probe 6 is placed in contact with the material to be transferred, thereby causing it to be attracted to the probe. The material can then be lifted to a new location. When the material is correctly located, the valve member 23 is depressed so that the equipment is switched to the irrigating mode thereby causing the material to be forced off the end of the probe 6 by the pressure of fluid within it. Minor blockages that might occur in the suction mode can be cleared by changing to the irrigation mode so that the obstruction is forced out of the probe 6.

Because only a single bore outlet conduit and probe are used, this can be narrower than previous double conduit arrangements thereby making the equipment easier to use in restricted places.

Various alternative valves could be used and the housing of the entire euqipment could be made as a single moulding. The valve could be located remote from the operating tip of the equipment and connected with the tip by a length of flexible tubing. Alternative materials, such as metals, could be used in the construction of the equipment.

What we claim is:

1. Medico-surgical suction irrigation equipment adapted to be hand held and including a handle; a first bore extending through said handle, said first bore having a pair of spaced ends located respectively adjacent spaced portions of said handle; means for connecting one end of said first bore to a suction source; a second bore extending through said handle in spaced relation to said first bore, said second bore having a pair of spaced ends located respectively adjacent spaced portions of said handle; means for connecting one end of said second bore to a source of irrigating fluid; valve means comprising a valve housing attached to said handle for connecting said valve means with the other ends of said first and second bores; said valve housing having a single outlet port; a valve member within said housing, said valve member being movable between first and second positions in said housing and having a reduced diameter waist section around which fluid flows through said housing in each of said first and second valve member positions, said valve member being connected to a depressible actuator member located adjacent said handle external of said housing; spring means located within said housing, said spring means urging said valve member upwardly in said valve housing to said first position, said valve member being so disposed relative to said handle that said valve member can be displaced downwardly along said housing against the action of said spring means transversely of said bores by pushing down on said actuator member with the finger or thumb of a user of the equipment while said user is holding said equipment at said handle, said downward displacement of the valve member being operative to move said valve member from said first position to said second position relative to said outlet port thereby to connect a selected one of said first or second bores to said outlet port around the said waist section of said valve member such that said outlet port either applies suction or supplies irrigating fluid from said selected one of said bores, said spring means displacing said valve member upwardly from said second position to said first position when said actuator member is released by the user's finger or thumb such that the other of said bores is connected to said outlet port around the same said waist section of said valve member so that said outlet port then either supplies irrigating fluid or applies suction from said other bore.

2. Suction-irrigation equipment according to claim 1, including a probe member and means removably coupling said probe member with said outlet port.

3. Suction-irrigation equipment according to claim 1, wherein said handle is of elongated configuration, said first bore and said second bore extending substantially parallel to one another through said handle in the direction of elongation of said handle, and said outlet port extending from said valve housing substantially parallel with said first and second bores.

4. Suction-irrigation equipment according to claim 3, wherein said first and second bores, and said outlet port are located on opposite sides of said valve housing.

5. Suction-irrigation equipment according to claim 4, wherein said outlet port is located intermediate said first and second conduits.

* * * * *